(12) United States Patent
Solomon et al.

(10) Patent No.: US 8,696,610 B2
(45) Date of Patent: Apr. 15, 2014

(54) MAGNETORHEOLOGICAL MEDICAL BRACE

(76) Inventors: Clifford T. Solomon, Severna Park, MD (US); Theodore C. Solomon, Hampstead, MD (US)

( * ) Notice: Subject to any disclaimer, the term of this patent is extended or adjusted under 35 U.S.C. 154(b) by 94 days.

(21) Appl. No.: 13/556,112

(22) Filed: Jul. 23, 2012

(65) Prior Publication Data

US 2013/0023720 A1    Jan. 24, 2013

Related U.S. Application Data

(60) Provisional application No. 61/510,432, filed on Jul. 21, 2011.

(51) Int. Cl.
*A61F 5/00* (2006.01)
*A61F 13/00* (2006.01)

(52) U.S. Cl.
USPC .......... 602/5; 602/6; 602/23; 602/60; 602/61; 602/62; 600/15

(58) Field of Classification Search
CPC ........ A61N 2/02; A61N 2/008; A61F 5/0585; A61F 5/0111; A61F 5/0123; A61F 5/0125; A61F 13/00; A61F 13/04; A61F 13/08; A61F 13/14; A61F 7/007
USPC ............. 602/2, 5, 6, 23, 26, 60–63; 600/9, 15
See application file for complete search history.

(56) References Cited

U.S. PATENT DOCUMENTS

| 7,393,364 B2 | 7/2008 | Martin |
| 7,455,696 B2 | 11/2008 | Bisbee, III et al. |
| 7,507,215 B2 | 3/2009 | Ryan |
| 7,659,636 B2 | 2/2010 | Donelan et al. |
| 7,691,154 B2 | 4/2010 | Asgeirsson et al. |
| 7,892,630 B1 | 2/2011 | McKnight et al. |
| 8,277,402 B2 * | 10/2012 | Chisena et al. ................. 602/20 |

(Continued)

FOREIGN PATENT DOCUMENTS

| CN | 101251169 A | 8/2008 |
| DE | 198 20 570 A1 | 11/1999 |
| KR | 2002-0067440 | 8/2002 |
| WO | WO 2007/125148 A1 | 11/2007 |

OTHER PUBLICATIONS

A passive and a semi-active orthopedic knee brace, Farzad Ahmadkhanlou, The Ohio State University website:http://etd.ohiolink.edu/send-pdf.cgi/Ahmadkhanlou%20Farzad.pdf?osu1212419874.

(Continued)

*Primary Examiner* — Kim M Lewis
(74) *Attorney, Agent, or Firm* — Steptoe & Johnson LLP (57) ABSTRACT

The magnetorheological (MAR) medical brace includes a flexible outer shell that fits around the anatomical area to be braced and a plurality of adjustable straps for securing the shell onto the anatomical area. The shell encases a MAR pack filled with magnetorheological fluid or gel. A plurality of magnets is attached to or encased in the shell to provide a magnetic field acting on the MAR pack. The interaction of the magnetic field with the MAR pack adjustably increases or decreases the stiffness of the shell depending on the strength of the magnetic field. A control mechanism is provided for selective adjustment of the magnetic field and other functions.

15 Claims, 6 Drawing Sheets

(56) References Cited

U.S. PATENT DOCUMENTS

| | | | |
|---|---|---|---|
| 8,579,842 B2* | 11/2013 | Majidi et al. | 602/5 |
| 2004/0126565 A1* | 7/2004 | Naganathan et al. | 428/323 |
| 2008/0065230 A1* | 3/2008 | Nordt et al. | 623/39 |
| 2008/0083140 A1 | 4/2008 | Ellis | |
| 2008/0300692 A1 | 12/2008 | Moser et al. | |
| 2009/0030530 A1 | 1/2009 | Martin | |
| 2010/0251574 A1 | 10/2010 | Battlogg et al. | |
| 2012/0035410 A1* | 2/2012 | Borgos et al. | 600/13 |

OTHER PUBLICATIONS

Leg brace with MR fluid brake, Dig Into TV website: http://www.diginfo.tv/2010/10/22/10/0202-r-en.php.

* cited by examiner

MAGNETORHEOLOGICAL MEDICAL BRACE

CROSS-REFERENCE TO RELATED APPLICATION

This application claims the benefit of U.S. Provisional Patent Application Ser. No. 61/510,432, filed Jul. 21, 2011.

FIELD OF THE INVENTION

The present invention relates to medical devices and particularly to a magnetorheological medical brace with controlled stiffness for optimal support and recovery.

DESCRIPTION OF THE RELATED ART

Any type of trauma or injury to a limb or bone requires a relatively long time to heal. In many cases, the physician usually recommends at least six weeks of recovery time. To ensure proper recovery, the limb or bone is immobilized either by braces, splints or a cast depending on the extent of damage. This stabilizes the bone or limb so as to prevent, in the case of broken bones, undesirable misalignment of the set bone or in the case of sprains or other types of injuries, any movement that may cause further injury or unnecessary pain. While such measures are quite sufficient, the immobilized limb and the surrounding muscles tend to atrophy due to lack of physical movement. It is not unusual for a patient to struggle through a post-recovery regimen of physical exercise or therapy in order to gain the prior musculature and strength in the injured anatomy.

Another complication to such healing is a matter of comfort and convenience. As the patient endures the period of healing, the recovering area tends to itch, which is usually a positive symptom that recovery is going well. However, for some types of braces, it may be challenging for the patient to reach the agitated area to scratch, which often ends in frustration and irritation. For some, it may even reach unendurable proportions such that the patient is forced to remove the brace, splint or cast, which can jeopardize the healing progress. Moreover, attempts to clean the injured limb can be challenging. Since removal of the brace, splint or cast prior to complete healing is not usually recommended, the patient typically forgoes cleaning of the injured area during the period of recovery. This can lead to unsightly accumulation of dirt and grime or potential infections, especially for patients who had undergone surgery for the injury.

In order to accelerate healing, re-strengthening of the injured area and increase comfort and convenience for the patient, it would be more effective for a brace, splint or cast to be progressively loosened during the period of recovery such that the patient has some limited movement for exercising the limb as the limb heals, at least for a relatively short period of time. This can be conventionally facilitated by frequent visits to the health care facility for doctor consultation and replacement or adjustment of the medical device. However, frequent visits can be costly in terms of finances and time.

Sports braces such as those for the joints, e.g., ankles, wrists, knees and elbows, also suffer from similar effectiveness deficiencies. Most sports braces do not have any means of selectively increasing or decreasing the stiffness of the brace. The inherent stiffness of a prescribed sports brace may be sufficient for most, but it could be problematic for those suffering from weak joints or other joint related complications. For example, the stiffness of the brace may dramatically hinder movement, which decreases the benefits of the sports activity and/or the enjoyment thereof. Moreover, as time passes, the user may require more or less support from the brace due to extended movement of the joint or from physical expenditure.

In light of the above, it would be a benefit in the medical arts to provide an immobilizing device with adjustable stiffness for more effective healing, support, convenience and comfort. Thus, a magnetorheological medical brace having easily adjustable stiffness is needed to solve the aforementioned problems.

SUMMARY OF THE INVENTION

The magnetorheological (MAR) medical brace includes a flexible outer shell that fits around the anatomical area to be braced and a plurality of adjustable straps for securing the shell onto the anatomical area. The shell encases a MAR pack filled with magnetorheological fluid or gel. A plurality of magnets is attached to or encased in the shell to provide a magnetic field acting on the MAR pack. The interaction of the magnetic field with the MAR pack adjustably increases or decreases the stiffness of the shell depending on the strength of the magnetic field. A control mechanism is provided for selective adjustment of the magnetic field and other functions.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The magnetorheological medical brace, a first embodiment of which is generally referred to by the reference number 10, provides adjustable stiffness and other features for optimum support, convenience and comfort. The phrase "magnetorheological medical brace" will hereinafter be referred to as "MAR medical brace." In the exemplary embodiment shown in FIGS. 1 and 2, the MAR medical brace 10 may be a leg brace 12 having an elongate shell or cover 14 adapted to be wrapped around the user's leg L. The shell 14 is substantially semi-cylindrical or semi-frustoconical in shape so that the shell 14 may easily wrap around and conform to the anatomy of leg L. The shell 14 is also relatively stiff or rigid to provide minimum support, as well as to retain the general shape of the shell 14. However, the shell 14 should also be flexible to allow for some movement without much effort. The shell 14 may be constructed from resilient, polymeric foam with some relative stiffness for minimum rigidity. Other materials such as neoprene, cushioned mats, elastomers, steel, plastics and combinations thereof may also be used as needed for some components of the brace.

Figure 1:
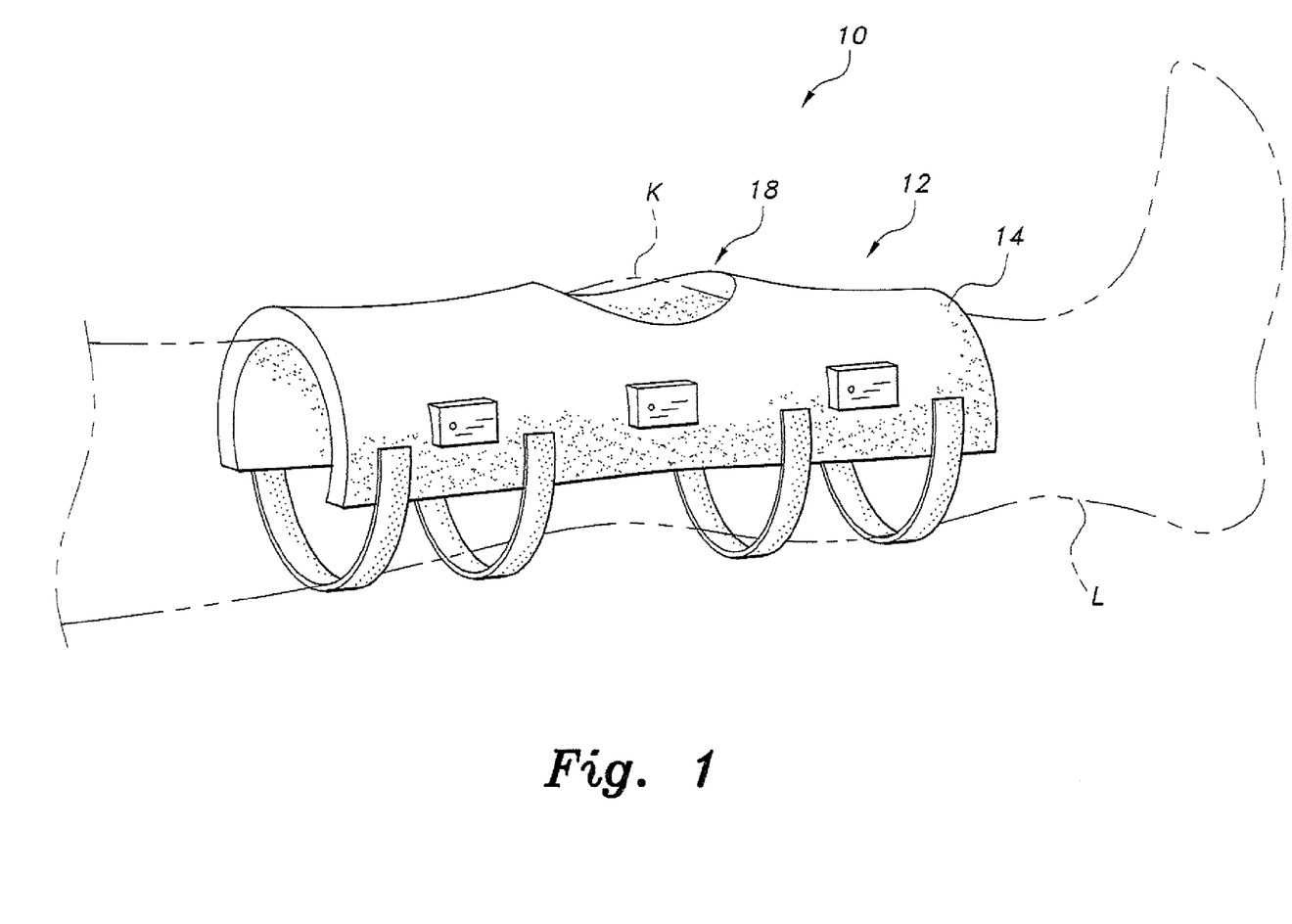
FIG. 1 is an environmental, perspective view of a magnetorheological medical brace according to the present invention.
Figure 2:
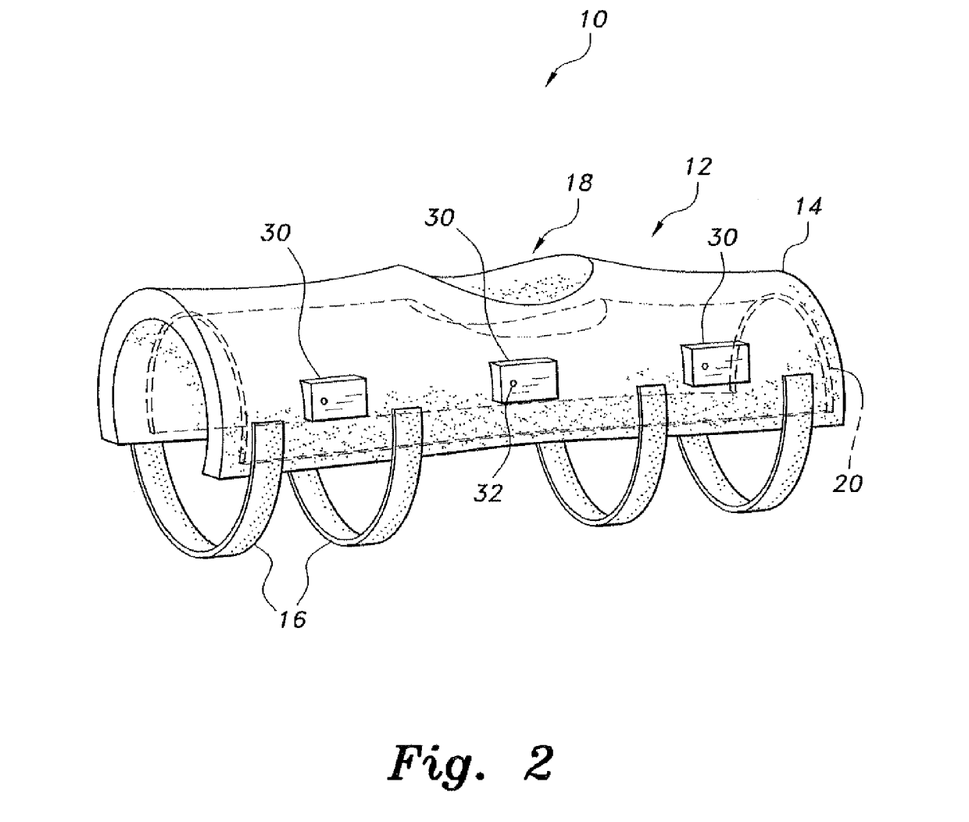
FIG. 2 is a perspective view of the magnetorheological medical brace according to the present invention.

The shell 14 can include a central through hole 18 where a patient's or user's knee joint K may protrude. The hole 18 permits flexing of the knee without encumbrance. A plurality of adjustable attachment connectors, such as straps 16, may be disposed at spaced intervals along the length of the shell 14. These straps 16 secure the shell 14 onto a wide range of leg girths. The straps 16 may be secured to the user by hook and loop fasteners, buckles, snap-fit fasteners or any other type of adjustable connectors.

To facilitate adjustable stiffening of the leg brace 12, the shell 14 includes a magnetorheological (MAR) cell, tube or pack 20 disposed inside the shell 14. The MAR pack 20 is preferably a packet or durable balloon filled with magnetorheological material in fluid or gel form. MAR material is a substance that can vary the material yield stress characteristics when exposed to a magnetic field. In other words, the stillness or rigidity of the MAR pack 20 varies, depending on the strength of magnetic forces acting thereon. Thus, whenever the MAR pack 20 experiences some degree of magnetic force or field, the whole leg brace 12 correspondingly stiffens or loosens proportionately to the overall rigidity of the MAR pack 20. One example of such a MAR material is a combination of carbonyl iron powder and silicone oil. It is to be understood that other MAR materials may also be used for the MAR pack 20. In the preferred embodiment, the leg brace 12 is of unitary construction formed in a molding process with the MAR pack 20 embedded within the shell 14. As an alternative, the MAR pack 20 may be removably inserted inside a cavity within the shell 14.

The magnetic force or field may be supplied by a plurality of magnet packs, consoles or terminals 30 disposed on one or both sides of the leg brace 12. Each magnet pack 30 can include a permanent magnet or an electromagnet of a given strength. In a preferred embodiment, the magnet packs 30 are magnetically shielded on the outside to ensure that magnetic forces influence the MAR material, rather than anything else that may be nearby. When using permanent magnets, the physician or the user may selectively change one for another of higher or lower strength to adjust the of stiffness of the MAR medical brace 10. Similar results may be obtained with an electromagnet by using a control mechanism to adjust the magnetic field strength, an example of which will be described below.

In the preferred embodiment, the control mechanism 40 may be disposed in one of the magnet packs 30. As shown schematically in FIG. 6, the control mechanism 40 includes a processor 42 for controlling the various functions of the control mechanism 40 and is connected to a power source 44 supplying power to the control assembly 40 and the electromagnets in the other magnet packs 30. In a preferred embodiment, the power source 44 can be a rechargeable and reusable battery, such as lead-acid, nickel cadmium (NiCd), nickel metal hydride (NiMH), lithium ion (Li-ion), and lithium ion polymer (Li-ion polymer). As an alternative, the power may be supplied directly from an AC source. To adjust the strength of the electromagnet, the user can increase or decrease the amount of power being supplied to the MAR pack 20 via the processor 42 to thereby selectively strengthen or weaken the magnetic field. The magnet pack 30 may include an indicator light or display 32 that provides information about the operations of the control mechanism 40, e.g., ON, OFF and/or remaining power.

Figure 6:
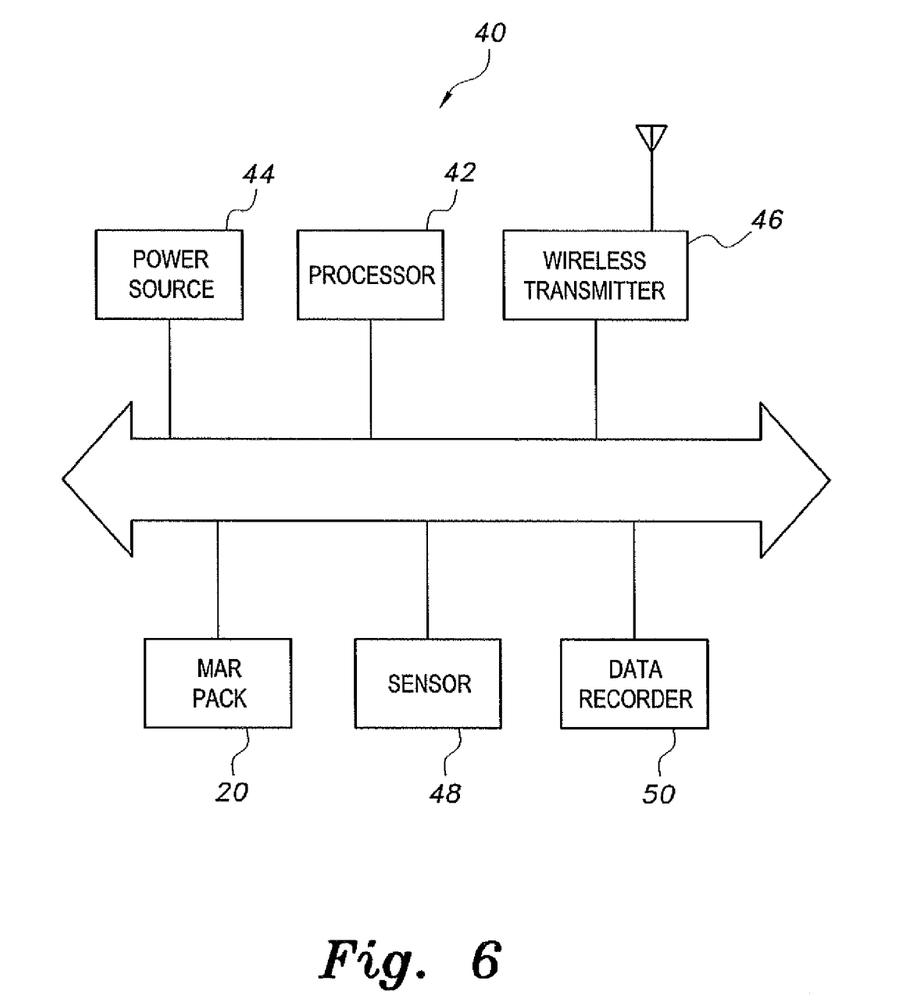
FIG. 6 is a schematic diagram of the controls for a magnetorheological medical brace according to the present invention.

In addition to the basic control of the magnetic field or force, the control mechanism 40 includes other features to help monitor the patient's or user's healing and/or exercise progress. The control mechanism 40 can include a sensor 48 that senses various activities such as the frequency of wear, the intensity of the magnetic field, the frequency of limb movement, etc. This data may be recorded on the data recorder 50 and transmitted wirelessly via the wireless transmitter 46 to a monitoring station, such as a central database in a health care facility or to a personal computer. The recorded and transmitted data helps the physician or user calculate and determine physical activity goals as part of the healing process. Moreover, the data may be used to monitor the user's adherence with the physician's recommendations. For example, if the physician prescribed a strict guideline and duration of wearing the leg brace 12 and the patient fails to comply, as evidenced by prolonged periods of recorded inactivity, the transmitted data will note the lapse and alert the physician. Then the physician may follow up with the patient in a timely manner to determine the cause. As an alternative, the data stored in the data recorder 50 may be retrieved at the end of a given period of time instead of being transmitted by the wireless transmitter 46, especially for those who live in areas where wireless communication is not available.

Data transmission and the data itself may be compromised by the magnets used in the MAR medical brace 10. The magnets may cause magnetic interference, which can reduce the clarity of transmission from the wireless transmitter 46 and potentially damage the data recorded on the data recorder 50. Since the control mechanism 40 will be subject to magnetic interference from the magnets and/or electromagnets, at least the wireless transmitter 46 and the data recorder 50 are preferably magnetically shielded to overcome potential magnetic interference.

While the above describes some of the user or patient defined adjustment of the stiffness of the MAR medical brace 10, the control mechanism 40 includes programming capabilities that may be preset by the physician or possibly the user. For example, the physician may program the MAR medical brace 10 via the processor 42 to gradually decrease the magnetic strength from the magnet packs 30 over the course of the recommended healing or recovery time. This results in the stiffness or rigidity of the MAR medical brace 10 gradually decreasing as the patient heals and grows stronger over time, which eliminates frequent visits with the physician for similar adjustments. Moreover, the wireless transmitter 46 may also function as a receiver in order to receive programs, physician directed adjustments and other commands remotely. In the case of the MAR medical brace 10 being worn for sports or recreational physical activity, the MAR medical brace 10 may be programmed by the user to increase the stiffness over a user-defined period of time so that proper support is maintained as the user becomes physically fatigued from that activity. This relieves constant manual readjustments from the user.

Figure 3:
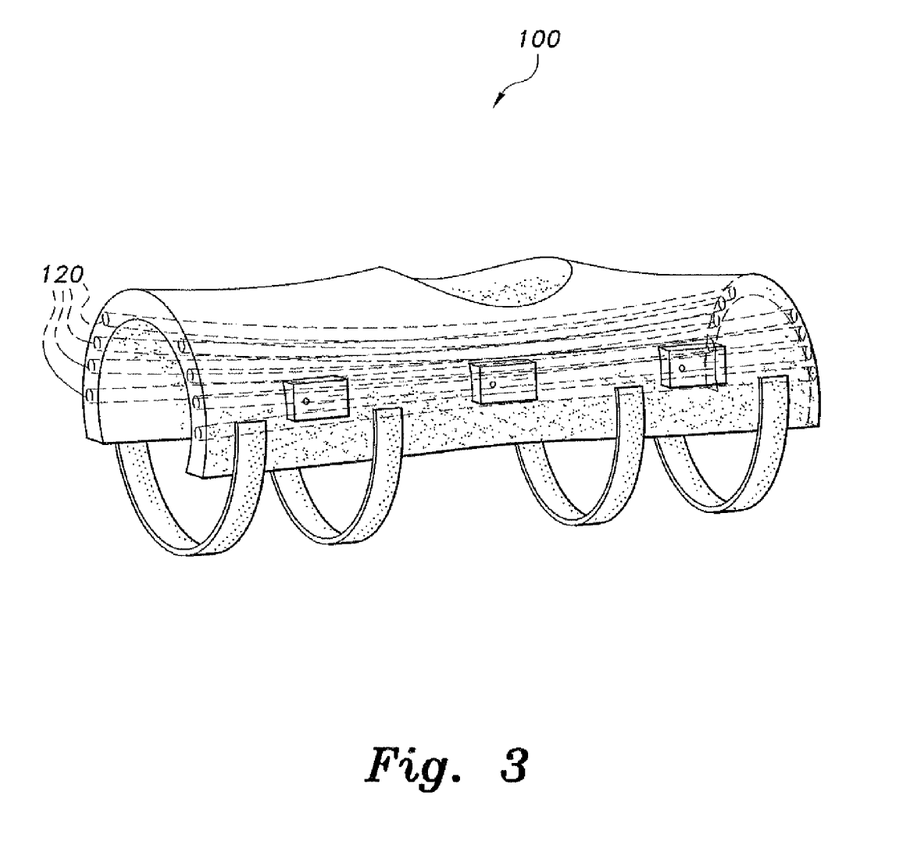
FIG. 3 is a perspective view of an alternative embodiment of a magnetorheological medical brace according to the present invention.
Figure 4:
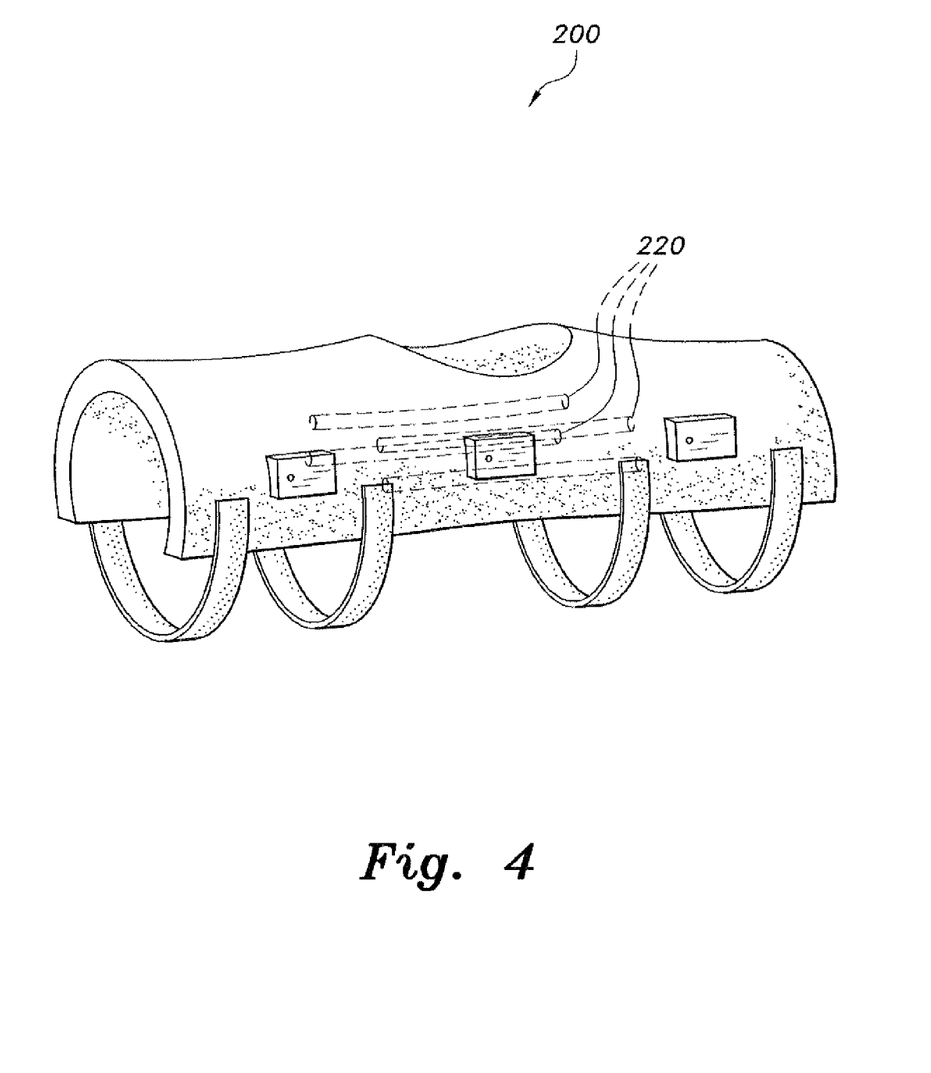
FIG. 4 is a perspective view of another alternative embodiment of a magnetorheological medical brace according to the present invention.
Figure 5:
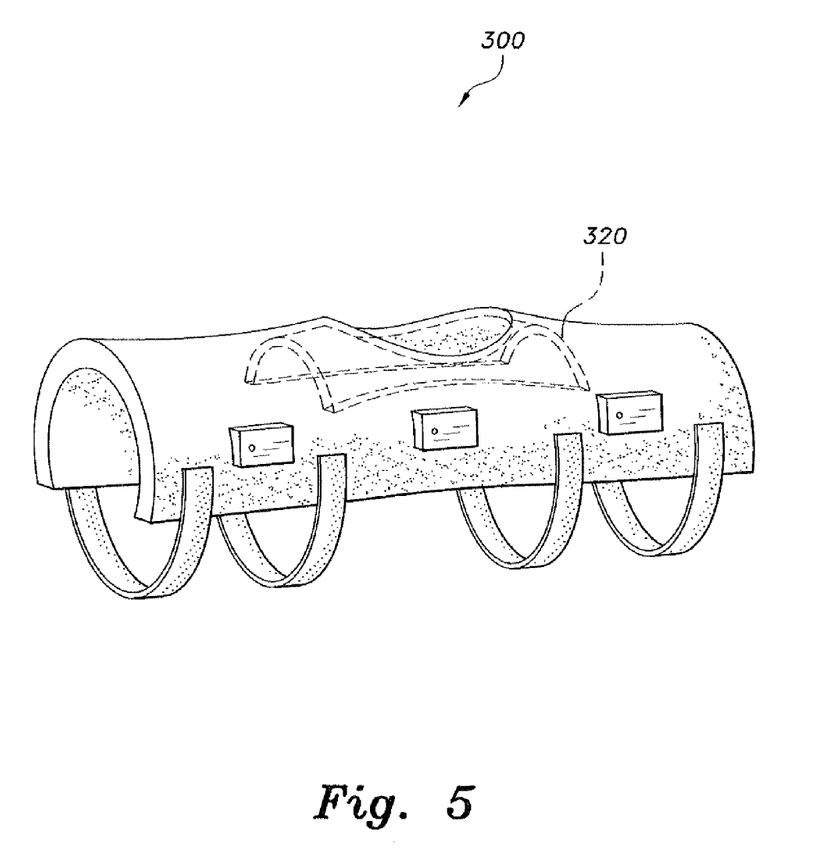
FIG. 5 is a perspective view of a still further alternative embodiment of a magnetorheological medical brace according to the present invention.

Referring to FIGS. 3-5, these drawings show alternative arrangements of the MAR pack for selective reinforcement of the brace. In FIG. 3, the MAR medical brace 100 in the form of a leg brace includes a plurality of MAR packs 120 embedded in the shell. The MAR packs 120 are shaped as elongate rods for longitudinal reinforcement of the MAR medical brace 100. The MAR packs 120 are removably inserted into the shell. As an alternative, the elongate MAR packs 120 may be molded with the shell. In FIG. 4, the MAR medical brace 200 includes a plurality of relative short MAR packs 220 disposed inside the shell. These MAR packs 220 may be placed in a variety of select locations on the MAR medical brace 200 wherever selective stiffening is desired. In FIG. 5, the MAR medical brace 300 includes a MAR pack 320 that is relatively smaller than the one shown in FIG. 2. The configuration thereof provides adjustable stiffness in a localized area around the joint. The variety of different MAR pack configurations is subject only to the changing needs of the patient.

Thus, it can be seen that the MAR medical brace 10, 100, 200, 300 is a highly adjustable brace that promotes optimum healing, convenience and comfort for the user. The MAR packs 20, 120, 220, 320 provide an easy and simple means of adjusting the stiffness and rigidity of the brace for increased comfort and freedom of movement as needed while maintaining the necessary support. The unitary and relatively simple construction also allows the MAR medical brace 10, 100, 200, 300 to be easily and inexpensively manufactured. In addition, the control mechanism 40 provides increased functionality whereby the patient's progress can be easily monitored and tailored to the individual.

It is to be understood that the MAR medical brace 10, 100, 200, 300 encompasses a variety of alternatives. For example, although the exemplary embodiments above describes the MAR medical brace 10, 100, 200, 300 in terms of a leg brace, it is to be understood that the teachings thereof equally applies to all types of braces. Moreover, the control assembly 40 is not limited to being installed in one of the magnet packs 30. Instead, the control assembly 40 can be a separate module or remote that can be carried by the user. Furthermore, it is to be understood that the MAR medical brace 10, 100, 200, 300 is not limited to human subjects or patients. The MAR medical brace 10, 100, 200, 300 may also be used on other subjects, such as animals.

It is to be understood that the present invention is not limited to the embodiments described above, but encompasses any and all embodiments within the scope of the following claims.

We claim:

1. A magnetorheological (MAR) medical brace, comprising:
   a flexible outer shell having an ergonomic shape adapted to be wrapped around an area of a user's anatomy, the shell having an inherent degree of stiffness;
   a plurality of adjustable connectors attached to the shell for securing the shell on the user's anatomy;
   at least one MAR pack disposed inside the outer shell, the at least one MAR pack being filled with magnetorheological material, the at least one MAR pack having an inherent degree of stiffness;
   a plurality of magnet packs attached to the shell at spaced locations, each magnet pack having a magnet capable of exerting a magnetic field of a predetermined strength, the magnets exposing the MAR pack to magnetic field forces adjustably stiffening or loosening the magnetorheological material; and
   means for selectively adjusting the magnetic field strength of the magnets;
   wherein selective adjustment of the magnetic field strength of the magnets increases or decreases the degree of stiffness of the shell to thereby provide adjustable rigidity for optimum healing and support.

2. The magnetorheological medical brace according to claim 1, wherein said flexible outer shell comprises at least one material selected from the group consisting of resilient, polymeric foam, neoprene, cushioned mats, elastomers, steel, and plastics.

3. The magnetorheological medical brace according to claim 1, wherein said plurality of adjustable connectors comprises a plurality of straps having fasteners for connecting each strap.

4. The magnetorheological medical brace according to claim 3, wherein said fasteners comprises hook and loop fasteners.

5. The magnetorheological medical brace according to claim 1, wherein said at least one MAR pack comprises at least one packet embedded in said flexible outer shell, said at least one packet having said magnetorheological material contained therein, the magnetorheological material being a fluid.

6. The magnetorheological medical brace according to claim 5, wherein said magnetorheological material comprises a combination of at least carbonyl iron powder and silicone oil.

7. The magnetorheological medical brace according to claim 6, wherein said at least one packet comprises a shape substantially the same as said flexible outer shell, the packet having smaller dimensions than said shell.

8. The magnetorheological medical brace according to claim 6, wherein said at least one packet comprises a plurality of elongate rod-shaped packets disposed at select locations inside said flexible outer shell, said plurality of elongate rod-shaped packets providing longitudinal structural reinforcement for said flexible outer shell.

9. The magnetorheological medical brace according to claim 6, wherein said at least one packet comprises a plurality of short, elongate rod-shaped packets disposed at select locations inside said flexible outer shell, said plurality of short, elongate rod-shaped packets providing structural reinforcement for said flexible outer shell at select locations thereof.

10. The magnetorheological medical brace according to claim 1, wherein said magnet comprises a permanent magnet.

11. The magnetorheological medical brace according to claim 10, wherein said means for selectively adjusting comprises interchangeable permanent magnets, each of the interchangeable permanent magnets having a different magnetic strength.

12. The magnetorheological medical brace according to claim 1, wherein said magnet comprises an electromagnet.

13. The magnetorheological medical brace according to claim 12, wherein said means for selectively adjusting comprises a controller having means for selectively increasing and decreasing power applied to the electromagnet in order to provide commensurate change the magnetic strength of the electromagnet.

14. The magnetorheological medical brace according to claim 1, wherein said controller further comprises a sensor for generating data, means for recording data from the sensor, and a means for wireless transmission of the data.

15. A method of bracing a skeletal structure of a subject, the method comprising the steps of:
   placing a magnetorheological (MAR) medical brace on the subject's body, the brace having:
      a flexible outer shell having an ergonomic shape adapted to be wrapped around an area of a subject's anatomy, the shell having an inherent degree of stiffness;
      a plurality of adjustable connectors attached to the shell for securing the shell on the subject's anatomy;
      a MAR pack disposed inside the outer shell, the MAR pack being filled with magnetorheological material, the MAR pack having an inherent degree of stiffness;
      a plurality of magnet packs attached to the shell at spaced locations, each magnet pack having a magnet capable of exerting a magnetic field of a predetermined strength, the magnets exposing the MAR pack to magnetic field forces which adjustably stiffen or loosen the magnetorheological material; and a controller having means for selectively adjusting the magnetic field strength of the magnets;

wherein selectively adjusting of the magnetic field strength of the magnets increases and decreases the degree of stiffness of the shell to thereby provide adjustable rigidity for optimum healing and support;

activating the brace being worn by the subject; and adjusting the stiffness of the brace by controlling the strength of the magnetic field.

\* \* \* \* \*